United States Patent
Hu et al.

(10) Patent No.: US 9,688,687 B2
(45) Date of Patent: Jun. 27, 2017

(54) POLYMORPHIC FORMS OF ICOTINIB PHOSPHATE AND USES THEREOF

(71) Applicant: BETTA PHARMACEUTICALS CO., LTD., Yuhang, Hangzhou, Zhejiang (CN)

(72) Inventors: Shaojing Hu, Beijing (CN); Wei Long, Beijing (CN); Fei Wang, Beijing (CN); Yinxiang Wang, Beijing (CN); Lieming Ding, Beijing (CN)

(73) Assignee: BETTA PHARMACEUTICALS CO., LTD., Yuhang, Hangzhou, Zhejiang (CN)

( * ) Notice: Subject to any disclaimer, the term of this patent is extended or adjusted under 35 U.S.C. 154(b) by 0 days.

(21) Appl. No.: 14/896,706

(22) PCT Filed: Jun. 9, 2014

(86) PCT No.: PCT/CN2014/079488
§ 371 (c)(1),
(2) Date: Dec. 8, 2015

(87) PCT Pub. No.: WO2014/198211
PCT Pub. Date: Dec. 18, 2014

(65) Prior Publication Data
US 2016/0145262 A1 May 26, 2016

(30) Foreign Application Priority Data
Jun. 9, 2013 (WO) ............... PCT/CN2013/077091

(51) Int. Cl.
| | |
|---|---|
| C07D 491/056 | (2006.01) |
| A61K 31/519 | (2006.01) |
| A61K 45/06 | (2006.01) |
| C30B 7/00 | (2006.01) |
| C30B 7/14 | (2006.01) |
| C30B 29/54 | (2006.01) |

(52) U.S. Cl.
CPC ........ C07D 491/056 (2013.01); A61K 31/519 (2013.01); A61K 45/06 (2013.01); C30B 7/00 (2013.01); C30B 7/14 (2013.01); C30B 29/54 (2013.01); C07B 2200/13 (2013.01)

(58) Field of Classification Search
None
See application file for complete search history.

(56) References Cited

U.S. PATENT DOCUMENTS

| | | |
|---|---|---|
| 2011/0182882 A1 | 7/2011 | Wang et al. |
| 2014/0343082 A1 | 11/2014 | Wang et al. |
| 2014/0343283 A1 | 11/2014 | Hu et al. |
| 2016/0145262 A1 | 5/2016 | Hu et al. |

FOREIGN PATENT DOCUMENTS

| | | |
|---|---|---|
| CN | 1534026 A | 10/2004 |
| CN | 102911179 A | 2/2013 |
| EP | 2 392 576 A1 | 7/2011 |
| JP | 2003-519698 A | 6/2003 |
| WO | WO 03/082830 A1 | 10/2003 |
| WO | WO 2010/003313 A1 | 1/2010 |
| WO | WO2014/198211 A1 | 12/2014 |

OTHER PUBLICATIONS

McMahon et al. (2000).*
Pinedo et al. (2000).*
Berge et al.; "Pharmaceutical Salts"; *Journal of Pharmaceutical Sciences*, 66(1):1-19 (Jan. 1977).
Byrn et al.; "Pharmaceutical Solids: A Strategic Approach to Regulatory Considerations"; *Pharmaceutical Research*, 12(7):945-954 (1995).
Kawaguchi et al.; "Drug and Crystal Polymorphism"; *Journal of Human Environmental Engineering*, 4(2): 310-317 (2002).
Ooshima; "Crystallization of Polymorphs and Pseudo-polymorphs and Its Control"; *Pharm Stage*, 6(10):48-53 (Jan. 2007).
Takata; "API form screening and selection in drug discovery stage"; *Pharm Stage*, 6(10):20-25 (Jan. 2007).
Yamano; "Approach to Crystal Polymorph in Process Research of New Drug"; *Journal of Synthetic Organic Chemistry*, 65(9):907-913, 944 (Sep. 2007).

* cited by examiner

*Primary Examiner* — Paul V Ward
(74) *Attorney, Agent, or Firm* — Foley & Lardner LLP

(57) ABSTRACT

Disclosed is Icotinib phosphate (i.e., the compound of Formula (I)) and polymorph forms thereof, and methods of preparing and using them.

(I)

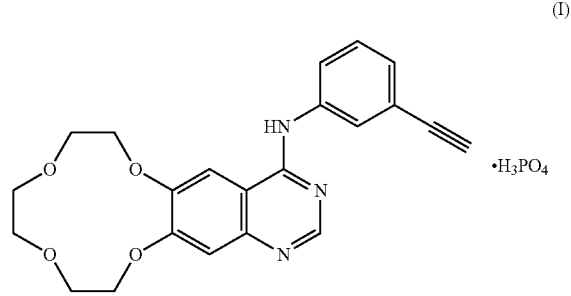

25 Claims, 5 Drawing Sheets

POLYMORPHIC FORMS OF ICOTINIB PHOSPHATE AND USES THEREOF

CROSS-REFERENCE TO RELATED APPLICATIONS

This application is a National Stage application of PCT/CN2014/079488, filed Jun. 9, 2014, which claims priority from International application PCT/CN2013/077091, filed Jun. 9, 2013.

FIELD OF THE INVENTION

The present invention relates to new polymorphic forms of Icotinib phosphate, processes for preparing these new polymorphic forms, pharmaceutical compositions thereof, and use of new polymorphic forms and pharmaceutical compositions for the treatment of cancer and cancer occurrence-related diseases.

BACKGROUND OF THE INVENTION

Tyrosine kinase receptors are trans-membrane proteins that, in response to an extracellular stimulus, propagate a signaling cascade to control cell proliferation, angiogenesis, apoptosis and other important features of cell growth. One class of such receptors, epidermal growth factor receptor (EGFR) tyrosine kinases, are overly expressed in many human cancers, including brain, lung, liver, bladder, breast, head and neck, esophagus, gastrointestinal, breast, ovary, cervix or thyroid cancer.

EGFR is expressed in many types of tumor cells. Binding of cognate ligands (including EGF, TGFα (i.e., Transforming Growth Factor-α) and neuregulins) to the extracellular domain causes homo- or heterodimerization between family members. The juxtaposition of cytoplasmic tyrosine kinase domains results in transphosphorylation of specific tyrosine, serine and threonine residues within each cytoplasmic domain. The formed phosphotyrosines act as docking sites for various adaptor molecules and subsequent activation of signal transduction cascades (Ras/mitogen-activated, PI3K/Akt and Jak/STAT) that trigger proliferative cellular responses.

Various molecular and cellular biology and clinical studies have demonstrated that EGFR tyrosine kinase inhibitors can block cancer cell proliferation, metastasis and other EGFR-related signal transduction responses to achieve clinical anti-tumor therapeutic effects. Two oral EGFR kinase inhibitors with similar chemical structures are Gefitinib (Iressa, AstraZeneca), approved by the U.S. FDA for advanced non-small cell lung cancer in 2003 (and later withdrawn), and Erlotinib Hydrochloride (Tarceva, Roche and OSI), approved by the U.S. FDA for advanced non-small cell lung cancer and pancreatic cancer treatment in 2004.

Many pharmaceutically active organic compounds can crystallize in more than one type of three-dimensional crystal structure. That is, the compounds may crystallize in different crystalline forms. This phenomenon (identical chemical structure but different crystalline structure) is referred to as polymorphism, and the species having different molecular structures are referred to as polymorphs.

Polymorphs of a particular organic pharmaceutical compound may have different physical properties, such as solubility and hygroscopicity, due to their distinct three-dimensional crystal structures. However, it is generally not possible to predict whether a particular organic compound will form different crystalline forms, let alone predict the structure and properties of the crystalline forms themselves. The discovery of a new crystalline or polymorph form of a pharmaceutically useful compound may provide a new opportunity for improving the overall characteristics of a pharmaceutical product. It enlarges the repertoire of materials that a formulation scientist has available for designing. It may be advantageous when this repertoire is enlarged by the discovery of new polymorphs of a useful compound.

Chinese Patent Publication No. CN1305860C discloses the structure of Icotinib (free base), on page 29, Example 15, Compound 23, and WO 2010/003313 disclosed Icotinib hydrochloride and its new crystalline polymorphs.

DESCRIPTIONS OF THE INVENTION

The present invention relates to Icotinib phosphate (i.e., the compound of Formula I), approximately pure polymorph forms thereof, and pharmaceutical acceptable salts thereof.

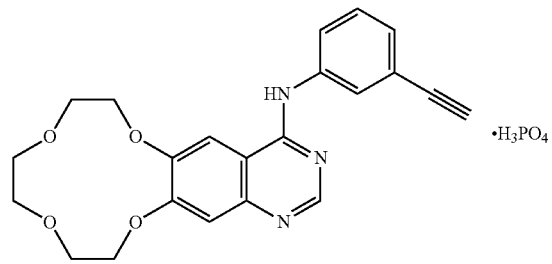

Formula I

In one aspect, the present invention provides Polymorph Form I of Icotinib phosphate.

In some embodiments, Polymorph Form I of Icotinib phosphate, when characterized by X-ray powder diffraction, has an X-ray diffraction pattern with characteristic peaks at diffraction angles 2θ of about 6.4°, 8.4°, 12.8°, 14.4° and 19.0°±0.2°.

In some embodiments, Polymorph Form I of Icotinib phosphate when characterized by X-ray powder diffraction, has an X-ray diffraction pattern with characteristic peaks at diffraction angles 2θ of about 6.4°, 8.4°, 12.8°, 14.4°, 19.0°, 20.7°, 22.7° and 25.7°±0.2°.

In some other embodiments, Polymorph Form I of Icotinib phosphate, when characterized by X-ray powder diffraction, has characteristic peaks, expressed in terms of the interplanar distance, at 13.7 Å, 10.5 Å, 6.9 Å, 6.1 Å and 4.7 Å.

In some other embodiments, Polymorph Form I of Icotinib phosphate, when characterized by X-ray powder diffraction, has characteristic peaks, expressed in terms of the interplanar distance, at 13.7 Å, 10.5 Å, 6.9 Å, 6.1 Å, 4.7 Å, 4.3 Å, 3.9 Å and 3.5 Å.

In some other embodiments, the X-ray powder diffraction pattern of Polymorph Form I is shown as in FIG. 1.

In one aspect, the present invention provides Polymorph Form II of Icotinib phosphate.

In some embodiments, Polymorph Form II of Icotinib phosphate, when characterized by X-ray powder diffraction, has an X-ray diffraction pattern with characteristic peaks at diffraction angles 2θ of 7.4°, 13.8°, 14.8°, 16.4° and 18.0°±0.2°.

In some embodiments, Polymorph Form II of Icotinib phosphate, when characterized by X-ray powder diffraction, has X-ray powder diffraction pattern with characteristic peaks at diffraction angles 2θ of 7.4°, 13.8°, 14.8°, 16.4°, 18.0°, 20.2°, 22.1° and 23.5°±0.2°.

In some embodiments, Polymorph Form II of Icotinib phosphate, when characterized by X-ray powder diffraction, has characteristic peaks expressed in terms of the interplanar distance, at 12.0 Å, 6.4 Å, 6.0 Å, 5.4 Å and 4.9 Å.

In some embodiments, Polymorph Form II of Icotinib phosphate, when characterized by X-ray powder diffraction, has characteristic peaks expressed in terms of the interplanar distance, at 12.0 Å, 6.4 Å, 6.0 Å, 5.4 Å, 4.9 Å, 4.4 Å, 4.0 Å and 3.8 Å.

In some other embodiments, the X-ray powder diffraction pattern of Polymorph Form II is shown as in FIG. 2.

In one aspect, the present invention provides Polymorph Form III of Icotinib phosphate.

In some embodiments, Polymorph Form III of Icotinib phosphate, when characterized by X-ray powder diffraction, has an X-Ray diffraction pattern with characteristic peaks at diffraction angles 2θ of 5.4°, 7.9°, 13.1°, 16.2° and 18.6°±0.2°.

In some embodiments, Polymorph Form III of Icotinib phosphate, when characterized by X-ray powder diffraction, has an X-Ray diffraction pattern with characteristic peaks at diffraction angles 2θ of 5.4°, 7.9°, 13.1°, 16.2°, 18.6°, 19.7°, 20.9° and 24.0°±0.2°.

In some embodiments, Polymorph Form III of Icotinib phosphate, when characterized by X-ray powder diffraction, has characteristic peaks expressed in terms of the interplanar distance, at 16.4 Å, 11.1 Å, 6.7 Å, 5.5 Å and 4.8 Å.

In some embodiments, Polymorph Form III of Icotinib phosphate, when characterized by X-ray powder diffraction, has characteristic peaks expressed in terms of the interplanar distance, at 16.4 Å, 11.1 Å, 6.7 Å, 5.5 Å, 4.8 Å, 4.5 Å, 4.3 Å and 3.7 Å.

In some other embodiments, the X-ray powder diffraction pattern of Polymorph Form III is shown as in FIG. 3.

In one aspect, the present invention provides Form IV of Icotinib phosphate.

In some embodiments, Polymorph Form IV of Icotinib phosphate, when characterized by X-ray powder diffraction, has an X-Ray diffraction pattern with characteristic peaks at diffraction angles 2θ of 6.1°, 8.0°, 14.7°, 17.3° and 18.3°±0.2°.

In some embodiments, Polymorph Form IV of Icotinib phosphate, when characterized by X-ray powder diffraction, has an X-Ray diffraction pattern with characteristic peaks at diffraction angles 2θ of 6.1°, 8.0°, 14.7°, 17.3°, 18.3°, 20.2°, 21.3° and 23.8°±0.2°.

In some embodiments, Polymorph Form IV of Icotinib phosphate, when characterized by X-ray powder diffraction, has characteristic peaks expressed in terms of the interplanar distance, at 14.5 Å, 11.0 Å, 6.0 Å, 5.1 Å and 4.8 Å.

In some embodiments, Polymorph Form IV of Icotinib phosphate, when characterized by X-ray powder diffraction, has characteristic peaks expressed in terms of the interplanar distance, at 14.5 Å, 11.0 Å, 6.0 Å, 5.1 Å, 4.8 Å, 4.4 Å, 4.2 Å and 3.7 Å.

In some other embodiments, the X-ray powder diffraction pattern of Polymorph Form IV is shown as in FIG. 4.

Polymorph Form I, II, III, or IV of the present invention can have a purity of ≥85%, ≥95%, or even ≥99%.

In still another aspect, the present invention provides processes for preparing a polymorph form of Icotinib phosphate, comprising reacting Icotinib with phosphoric acid in a reaction media, and isolating the polymorph form of Icotinib phosphate from the reaction media. The reaction between Icotinib and phosphoric acid, for example, can be carried out at the room temperature.

In some embodiments, the process for preparing a polymorph form of Icotinib phosphate, comprises reacting Icotinib with phosphoric acid in a reaction media including at least one solvent at room temperature.

In some embodiments of the process, the at least one solvent is chosen from THF, Dioxane, $H_2O$ or Acetone.

In some embodiments of the process, the media for reacting Icotinib with phosphoric acid may be a mixture of $H_2O$/THF or $H_2O$/acetone.

In some embodiments of the process, as a non-limiting example, the volume ratio between $H_2O$ and THF, or between $H_2O$ and Acetone may range from 1:10 to 1:30.

In some embodiments of the process, the media for reacting Icotinib with phosphoric acid is selected from THF, dioxane, $H_2O$/THF, and $H_2O$/acetone, and wherein the polymorph form of Icotinib phosphate isolated from the media is Form I of Icotinib phosphate.

In some embodiments of the process, the at least one solvent is selected from IPA, Acetone, ACN, 2-Butanone, or EtOH.

In some embodiments of the process, the at least one solvent is selected from IPA, Acetone, ACN, 2-Butanone, and EtOH, and wherein the polymorph form of Icotinib phosphate isolated from the media is Form II of Icotinib phosphate.

In some embodiments of the process, the molar ratio between phosphoric acid and Icotinib may range from 1:1 to 2:1 (e.g., 1:1, 1.5:1, 2:1).

In some embodiments of the process, the molar ratio between phosphoric acid and Icotinib is 1:1.

In some embodiments, the process for preparing a polymorph form of Icotinib phosphate, comprises at least one step choose from reverse anti-solvent crystallization from DMSO/EtOAc, anti-solvent crystallization from DMSO/EtOAc or DMF/DCM, or vapor diffusion from DMSO/IPAc or DMSO/MTBE.

In some embodiments of process, the step of anti-solvent crystallization from DMSO/EtOAc or DMF/DCM is carried out by dissolving Icotinib phosphate in DMSO or DMF to obtain a saturated solution, then adding EtOAc or DCM to the saturated solution, stirring the resulting solution for at least 2 hrs, and isolating the polymorph form of Icotinib phosphate.

In some embodiments of process, the step of reverse anti-solvent crystallization from DMSO/EtOAc is carried out by dissolving Icotinib phosphate in DMSO to obtain a saturated solution, adding the saturated solution into EtOAc, then stirring the resulting solution for at least 2 hrs and isolating the polymorph form of Icotinib phosphate.

In some embodiments of process, the step of vapor diffusion from DMSO/IPAc or DMSO/MTBE is performed by dissolving Icotinib phosphate in DMSO to get a saturated solution in a first container, placing the first container in a second container containing IPAc or MTBE, and inducing precipitation of Icotinib phosphate at room temperature.

In some embodiments, crystallization used herein to isolate Icotinib phosphate as set forth above can be carried out in a single solvent, or a mixture of solvents.

Suitable solvents for the crystallization to achieve isolation of a polymorph can be chosen from, but are not limited to, low carbon alcohols, ketones, ethers, esters, halogenated hydrocarbons, alkanes, halogenated benzene, aliphatic nitrile, and other aromatic solvents. As non-limiting example, the solvent for the crystallization of Icotinib phosphate can be chosen from isopropanol, ethyl acetate, 50% ethanol, water, N,N-dimethylformamide, methanol, ethanol, acetone, and propanol.

The crystallization of the polymorph forms of the present disclosure can be conducted in an appropriate solvent system comprising at least one solvent by evaporation, cooling and/or by addition of anti-solvents (solvents that are less able to solubilize the Icotinib phosphate than those described in the present invention) to achieve super-saturation in the solvent system.

As disclosed herein, crystallization may be done with or without seed crystals.

The individual crystalline forms disclosed herein can develop under specific conditions dependent on the particular thermodynamic and equilibrium properties of the crystallization process. Therefore, any persons of ordinary skill in the art of polymorphism in this area know that the formed crystals are a consequence of the kinetic and thermodynamic properties of the crystallization process. Under certain conditions (e.g., solvent, temperature, pressure, and concentration of the compound of this invention), a particular crystalline form may be more stable than another crystalline form (or in fact more stable than any other crystalline forms). However, the relatively low thermodynamic stability of particular crystals may have advantageous kinetics. Additional factors other than kinetics, such as time, impurity distribution, stirring, and the presence or absence of seed crystals, etc., may also affect the crystalline form.

In another aspect, the present invention provides a pharmaceutical composition comprising a therapeutically effective amount of at least one polymorph form of Icotinib phosphate disclosed herein and at least one pharmaceutically acceptable excipient, adjuvant or carrier.

The term "therapeutically effective amount" refers to the amount of a compound that, when administered to a subject for treating a disease, or at least one of the clinical symptoms of a disease or disorder, is sufficient to affect such treatment for the disease, disorder, or symptom. The "therapeutically effective amount" can vary depending on the compound, the disease, disorder, and/or symptoms of the disease or disorder, severity of the disease, disorder, and/or symptoms of the disease or disorder, the age of the subject to be treated, and/or the weight of the subject to be treated. An appropriate amount in any given instance can be apparent to those skilled in the art or can be determined by routine experiments. In the case of combination therapy, the "therapeutically effective amount" refers to the total amount of the combined active ingredient for the effective treatment of a disease, a disorder or a condition.

In some embodiments, the pharmaceutical composition comprises 0.01 wt %-99 wt % of at least one of the crystalline polymorphs disclosed herein.

In some embodiments, the pharmaceutical composition comprises 1 wt %-70 wt % of at least one of the crystalline polymorphs disclosed herein.

In some embodiments, the pharmaceutical composition comprises 10 wt %-50 wt % of at least one of the crystalline polymorphs disclosed herein.

The "pharmaceutically acceptable carrier" refers to conventional pharmaceutical carriers suitable for the desired pharmaceutical formulation, for example: a diluent, a vehicle such as water, various organic solvents, etc.; a filler such as starch, sucrose, etc.; a binder such as cellulose derivatives, alginates, gelatin and polyvinylpyrrolidone; a wetting agent such as glycerol; a disintegrating agent such as agar, calcium carbonate and sodium bicarbonate; an absorption enhancer such as quaternary ammoniums; a surfactant such as hexadecanol; an absorption carrier such as Kaolin and soap clay; a lubricant such as talc, calcium stearate, magnesium stearate, polyethylene glycol, etc. In addition, the pharmaceutical composition further comprises at least one other pharmaceutically acceptable excipient such as a decentralized agent, a stabilizer, a thickener, a complexing agent, a buffering agent, a diffusion enhancer, a polymer, a fragrance, a sweetener, and a dye. Preferably, the excipient is suitable for desired formulation and administration type.

In some embodiments, suitable pharmaceutical carriers are chosen from water, various organic solvents and various inert diluents or fillers. If necessary, the pharmaceutical compositions may further comprise one or more additives such as spices, adhesives and excipients. For oral administration, tablets can contain at least one excipient chosen, for example, from citric acid, a variety of disintegrant agents such as starch, alginic acid, and some silicates, and a variety of adhesives such as sucrose, gelatin and Arabic gum. In addition, lubricants including magnesium stearate and talc fillers may, for example, be used in the production of tablets. These components can also, for example, be used to formulate soft and hard gelatin capsules. When an aqueous suspension is needed for oral administration, the active compound may be mixed with at least one component chosen, for example, from a variety of sweeteners and flavoring agents, pigments, and dye combinations. If necessary, a variety of emulsifiers may be employed or suspensions generated; diluents such as water, ethanol, propylene glycol, glycerin, or their combination may also be utilized.

In some embodiments, the pharmaceutical composition further comprises at least one additional active ingredient other than Icotinib phosphate.

The pharmaceutical composition comprising the polymorph(s) of the present invention can be administrated via oral, inhalation, rectal, parenteral or topical administration to a subject who needs treatment. For oral administration, the pharmaceutical composition may be a regular solid formulation such as a tablet, powder, granule, a capsule and the like, a liquid preparation such as water or oil suspension or other liquid preparation such as syrup, solution, suspension or the like. For parenteral administration, the pharmaceutical composition may be solution, water solution, oil suspension concentrate, lyophilized powder or the like. As a non-limiting example, the formulation of the pharmaceutical composition disclosed herein is selected from tablet, coated tablet, capsule, suppository, nasal spray, and injection. In some embodiments, the formulation of the pharmaceutical composition disclosed herein is chosen from tablets and capsules.

In some embodiments, the pharmaceutical composition is suitable for oral administration.

In some embodiments, the pharmaceutical compositions disclosed herein may be administered orally in forms such as tablets, capsules, pills, powders, sustained release forms, solutions and/or suspensions; by non-intestinal injection in such form as a sterile solution, suspension or emulsion; through a local treatment form such as paste, cream, or ointment; or via a rectal form such as suppositories. The pharmaceutical compositions disclosed herein may be in a unit dosage form that is suitable for precise dosing applications.

In some embodiments, the pharmaceutical composition is in the form of tablets or capsules.

In some embodiments, the pharmaceutical composition of the present invention can be produced by known conventional methods in the pharmaceutical field. For example, one can mix the active ingredient with one or more excipients, and make the mixture into the target formulation.

In another aspect, the present invention provides uses of the polymorph form of Icotinib phosphate disclosed herein or the pharmaceutical composition thereof in the manufacturing of a medicament for the treatment or prevention in mammals of an excessive non-malignant hyperplasia disease, pancreatitis, kidney disease, cancer, angiogenesis or vascular occurrence-related illness, or for the mammalian embryo cell transplantation.

In some embodiments, the excessive non-malignant hyperplasia disease is benign skin hyperplasia or benign prostatic hyperplasia.

In some embodiments, the excessive non-malignant hyperplasia disease, pancreatitis, kidney disease, cancer, angiogenesis or angiogenesis-related disease is selected from: tumor angiogenesis, chronic inflammatory diseases, skin diseases, diabetic retinopathy, premature retinopathy, age-related degeneration stains, hemangioma, glioma, Kaposi Internal tumor, ovarian cancer, breast cancer, lung cancer, pancreatic cancer, lymphoma, prostate, colon and skin tumors and their complications.

In some embodiments, the skin disease is selected from psoriasis, scleroderma, or diabetes-induced skin diseases; and the chronic inflammatory disease is selected from rheumatoid arthritis or atherosclerosis.

In another aspect, the present disclosure provides a method for treating malignant tissue hyperplasia in mammals. This treatment method comprising administering a therapeutically effective amount of Icotinib phosphate and/or its crystalline forms and/or the pharmaceutical compositions disclosed above to mammals with hyperplasia disease. In some embodiments, the treatment method may also include the use of MMP (matrix metalloproteinase) inhibitor, VEGFR (vascular endothelial growth factor receptor) kinase inhibitors, HER2 inhibitor, VEGFR antibody drugs, and/or endostatin drugs. In some other embodiments, the treatment method also includes using one or more anti-tumor agents such as mitotic inhibitors, alkylating agents, anti-metabolites, tumor antibiotics, growth factor inhibitors, cell cycle inhibitors, enzymes, enzyme inhibitors, biological response modifiers, anti-hormone drugs and so on. The anti-tumor agents can be selected from carboplatin, paclitaxel, gemcitabine, methotrexate, 5-FU, camptothecin, cyclophosphamide, BCNU and other medications.

In some embodiments, the mammals being treated are humans.

In still another aspect, the present invention provides a method for treating a disease with excessive proliferation of mammalian tissues, comprising administering to a patient with the disease with a therapeutically effective amount of at least one polymorph form of Icotinib phosphate disclosed herein and/or the pharmaceutical composition thereof.

In some embodiments, the method further comprises administering to the patient at least one addition active ingredient selected from MMP inhibitors, VEGFR kinase inhibitors, HER2 inhibitors, VEGFR antibody drugs, or endostatin drugs.

In some embodiments, the method further comprises administering to the patient an anti-tumor agent selected from: mitotic inhibitors, alkylating agents, anti-metabolites, tumor antibiotics, growth factor inhibitors, cell cycle inhibitors, enzymes, enzyme inhibitors, biological response modifiers, or anti-hormones drugs.

In some embodiments, the method for treating a disease related to tyrosine kinase dysfunction comprises administering to a patient with the disease with a therapeutically effective amount of at least one polymorph form of Icotinib phosphate disclosed herein and/or the pharmaceutical composition thereof.

In some embodiments, the disease related to tyrosine kinase dysfunction is selected from the group consisting of brain, lung, liver, bladder, chest, head and neck, esophagus, gastrointestinal tract, breast, ovary, cervix or thyroid tumors and their complications.

In some embodiments of the method, the disease is selected from brain cancer, lung cancer (such as non-small cell lung cancer (NSCLC)), kidney cancer, bone cancer, liver cancer, bladder cancer, breast, head and neck cancer, esophageal cancer, stomach, colon, rectum cancer, breast cancer, ovarian cancer, melanoma, skin cancer, adrenal cancer, cervical cancer, lymphoma, or thyroid tumors and their complications.

In some embodiments, the methods set forth above may be applied in combination with any chemical therapy, biological therapy, and/or radiation therapy.

In some embodiments, the treatment method set forth above may further comprise application of anti-EGFR antibodies, anti-EGF antibodies, or both, in the same treatment.

In some embodiments, at least 85% of the Icotinib phosphate present in the pharmaceutical composition is in a crystalline form. As a non-limiting example, at least 85% of the Icotinib phosphate present in the pharmaceutical composition is at least one chosen from the polymorphs of Icotinib phosphate disclosed herein.

In some embodiments, at least 95% of the Icotinib phosphate present in the pharmaceutical composition is in a crystalline form. As a non-limiting example, at least 95% of the Icotinib phosphate present in the pharmaceutical composition is at least one chosen from the polymorphs of Icotinib phosphate disclosed herein.

In some embodiments, at least 99% of the Icotinib phosphate present in the pharmaceutical composition is in a crystalline form. As a non-limiting example, at least 99% of the Icotinib phosphate present in the pharmaceutical composition is at least one chosen from the polymorphs of Icotinib phosphate disclosed herein.

The term "approximately pure" as herein used refers to at least 85 wt %, such as at least 95 wt %, further such as at least 99 wt % of the compound of Formula I disclosed herein exists in a polymorph form of the present invention, particularly in the polymorph forms of Form I, Form II, Form III or Form IV.

The main peaks described in the crystalline polymorphs above are reproducible and are within the error limit (the specified value ±0.2).

In the present invention, "the X-ray powder diffraction pattern shown as in FIG. 1" refers to the X-ray powder diffraction pattern that show major peaks as in FIG. 1, wherein major peaks refer to those with the relative intensity greater than 10%, preferably greater than 30%, relative to the highest peak (with its relative intensity designated to be 100%) in FIG. 1. Likewise, in the present invention, the X-ray powder diffraction pattern shown as in FIG. 2, 3 or 4, refers to the X-ray powder diffraction pattern that show major peaks as in FIG. 2, 3, or 4, wherein major peaks refer to those with the relative intensity greater than 10%, preferably greater than 30%, relative to the highest peak (with its relative intensity designated to be 100%) in FIG. 2, 3, or 4, respectively.

DESCRIPTION OF THE EMBODIMENTS

Figure 1:
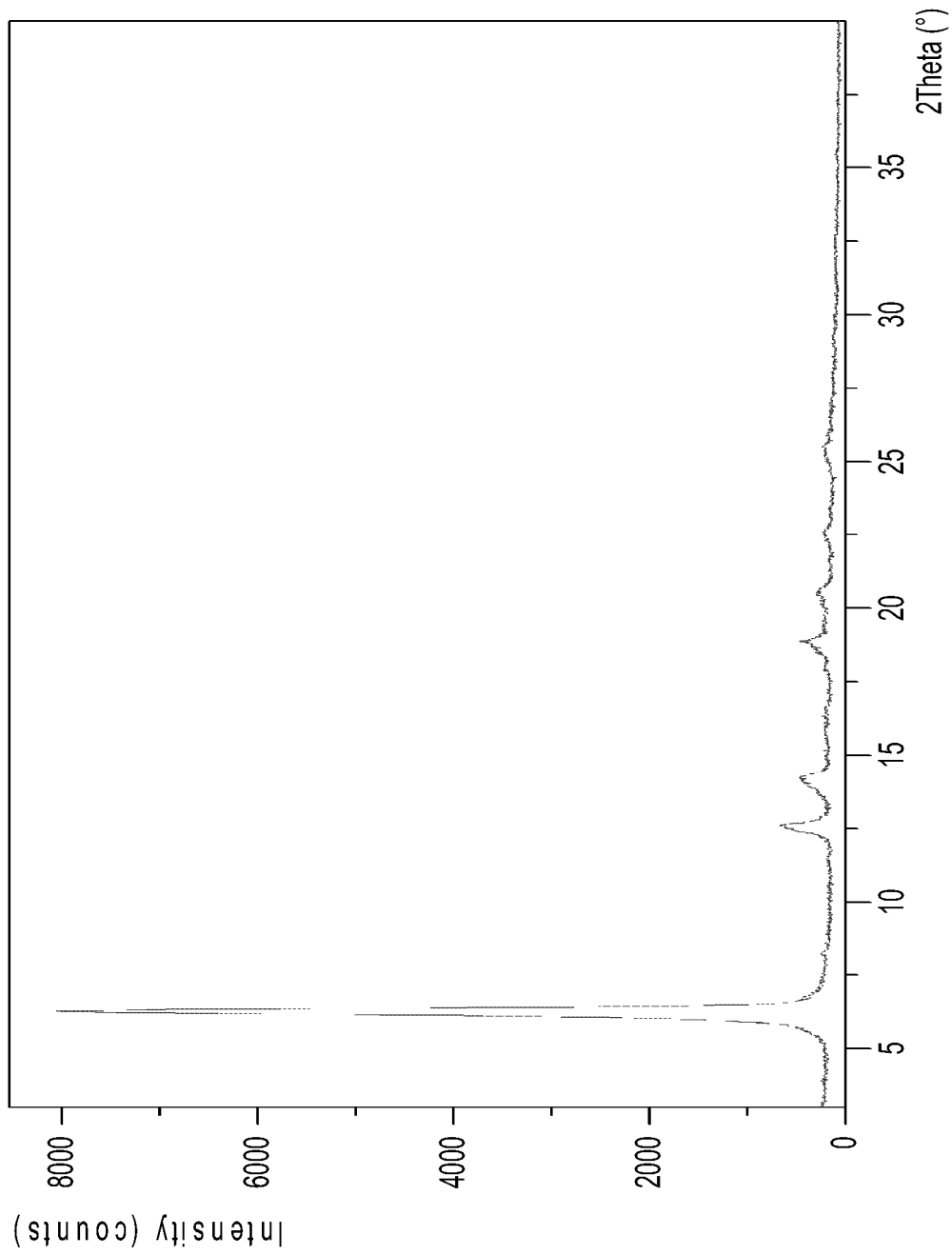
FIG. 1: The X-ray powder diffraction pattern of Polymorph Form I of the compound of Formula I.

The present invention is further exemplified, but not limited, by the following examples that illustrate the invention. The techniques or methods used in these examples, unless expressly stated otherwise, were conventional techniques or methods well known in the art.

The X-ray powder diffraction (XRPD) patterns for the crystalline forms of Icotinib phosphate were generated on a PANalytical X-ray Diffraction System with Empyrean console. The diffraction peak positions were calibrated using silicon powder which had a 2θ value of 28.443 degree. An Empyrean Cu LEF X-ray tube K-Alpha radiation was used as the source.

Abbreviations Used

RT: room temperature
THF: tetrahydrofuran
H$_2$O: water
IPA: isopropanol
ACN: acrylonitrile
EtOH: ethyl alcohol
IPAc: isopropyl acetate
DMSO: dimethylsulfoxide
EtOAc: ethyl acetate
MTBE: methyl tert-butyl ether
DMF: N,N-dimethylformamide
DCM: dichloromethane Example 1. Preparation of Polymorph Form I 100 g Icotinib hydrochloride was dissolved in a mixture of 300 ml ethanol and 200 ml water. A solution of 11.2 g sodium hydroxide in 100 ml water was added dropwisely at 60° C. to the Icotinib hydrochloride solution until the pH value of the reaction solution reached 13. The reaction solution was then stirred for 1 hr and then cooled down to the room temperature. The precipitate was filtered and washed with purified water and dried for 8 hrs under vacuum below 60° C. to obtain 90 g Icontinib.

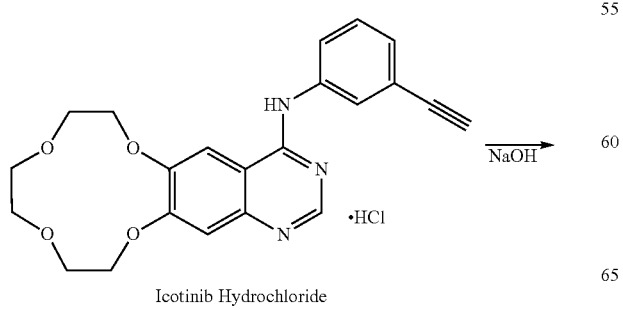

Icotinib Hydrochloride

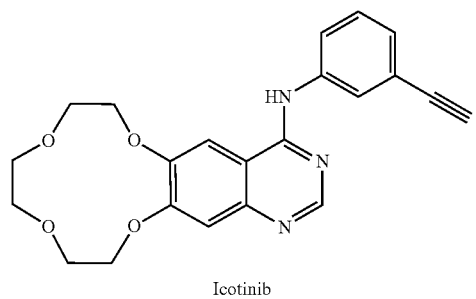

Icotinib

Polymorph Form I of Icotinib phosphate was obtained by reacting an Icontinib solution with a solution of phosphoric acid (1:1 molar ratio) in THF at the room temperature. Detail procedures as following: 10 mg Icontinib was dissolved in 1 ml THF, 18.9 μL phosphoric acid was also dissolved in 3 ml THF to provide a 0.1 mol/L phosphoric acid solution. 0.26 ml of the 0.1 mol/L phosphoric acid solution was then added to the Icontinib solution. The reaction mixture was stirred for 24 hrs, and then the Polymorph Form I was isolated.

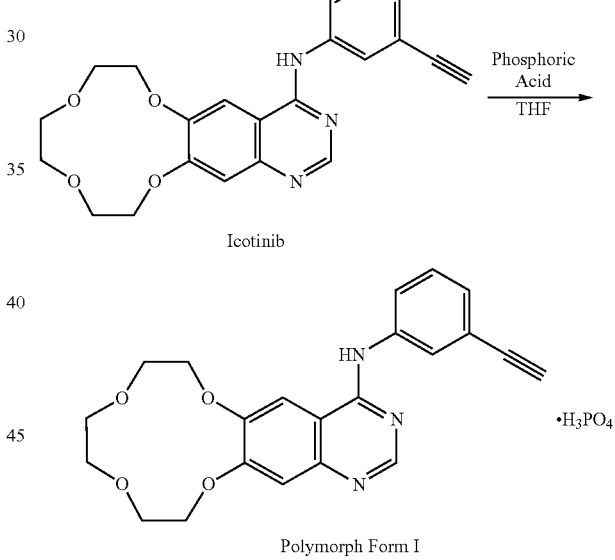

Example 2. Preparation of Polymorph Form I

Polymorph Form I was prepared by using the molar ratio of phosphoric acid and Icotinib 1.5:1 instead of 1:1 as Example 1 by following the same reaction conditions as described in Example 1.

Example 3. Preparation of Polymorph Form I

Polymorph Form I was prepared by using the molar ratio of phosphoric acid and Icotinib 2:1 instead of 1:1 as Example 1 by following the same reaction conditions as described in Example 1.

Example 4. Preparation of Polymorph Form I

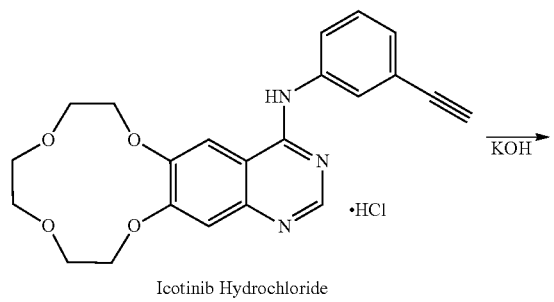

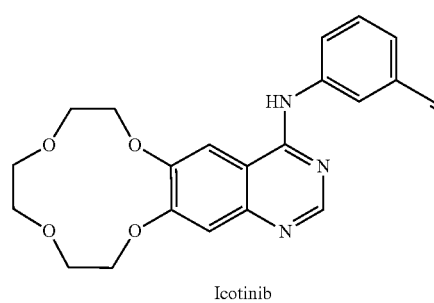

10 g Icotinib hydrochloride was dissolved in a mixture of 30 ml isopropanol and 20 ml water, a solution of 1.6 g potassium hydroxide in 10 ml water was added to the Ictotinob hydrochloride solution until the pH value of the reaction mixture reached 13. The reaction mixture was then stirred for 1-2 hrs before cooling down to the room temperature. The precipitate was filtered and washed with purified water and dried under vacuum for 8-10 hrs at a temperature below 50° C. to give 7.9 g Icontinib.

Polymorph Form I was obtained by reacting an Icontinib solution with a phosphoric acid solution (1:1 molar ratio) in dioxane at the room temperature. Detail procedures as following: 10 mg Icontinib was dissolved in 1 ml dioxane, 18.9 μL phosphoric acid was dissolved in 3 ml dioxane to obtain a 0.1 mol/L phosphoric acid solution. 0.26 ml of the 0.1 mol/L phosphoric acid solution was then added to the Icontinib solution. The reaction mixture was stirred for 24 hrs, and then the Polymorph Form I was isolated.

Example 5. Preparation of Polymorph Form I

A fifth sample of Polymorph Form I was prepared by using the molar ratio of phosphoric acid and Icotinib 1.5:1 instead of 1:1 as Example 4 by following the same reaction conditions as described in Example 4.

Example 6. Preparation of Polymorph Form I

A sixth sample of Polymorph Form I was prepared by using the molar ratio of phosphoric acid and Icotinib 2:1 instead of 1:1 as Example 4 by following the same reaction conditions as described in Example 4.

Example 7. Preparation of Polymorph Form I

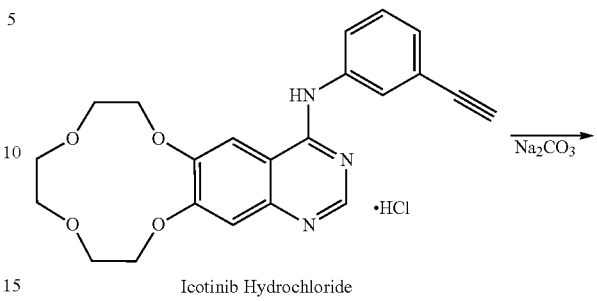

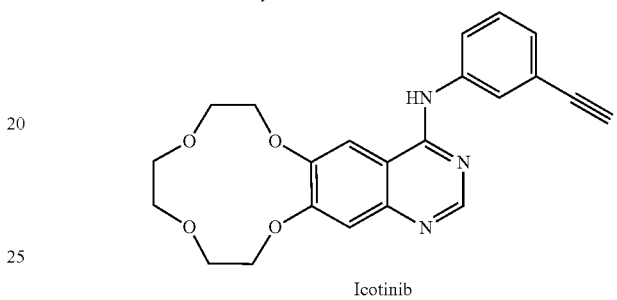

5 g Icotinib hydrochloride was dissolved in a mixture of 20 ml methanol and 15 ml water. To this Icotinib hydrochloride solution was then added dropwisely a solution of 1.5 g sodium carbonate in 10 ml water at 40° C. until the pH value of the mixture reached 13. The reaction mixture was then stirred for 1-2 hrs before cooling down to the room temperature. The precipitate was filtered and washed with purified water and then dried under vacuum for 8-10 hrs below 60° C. to give 4.0 g Icontinib.

Polymorph Form I of Icotinib phosphate was obtained by reacting an Icontinib solution with a phosphoric acid solution (1:1 molar ratio) in H$_2$O/THF (1:19, v/v) at the room temperature. Detail procedures as following: 10 mg Icontinib was dissolved in 1 ml H$_2$O/THF (1:19, v/v). 18.9 μL phosphoric acid was dissolved in 3 ml H$_2$O/THF (1:19, v/v) to obtain a 0.1 mol/L phosphoric acid solution. 0.26 ml of the 0.1 mol/L phosphoric acid solution was then added to the Icontinib solution and the reaction mixture was stirred for 24 hrs and then the Polymorph Form I was isolated.

Example 8. Preparation of Polymorph Form I

Polymorph Form I was prepared by using the molar ratio of phosphoric acid and Icotinib 1.5:1 instead of 1:1 as Example 7 by following the same reaction conditions as described in Example 7.

Example 9. Preparation of Polymorph Form I

Polymorph Form I was prepared by using the molar ratio of phosphoric acid and Icotinib 2:1 instead of 1:1 as Example 7 by following the same reaction conditions as described in Example 7.

Example 10. Preparation of Polymorph Form I

Polymorph Form I of Icotinib phosphate was prepared by using the Volume ratio of H$_2$O and THF 1:10 (i.e., H$_2$O/THF 1:10, v/v) instead of 1:19 as Example 7 by following the same reaction conditions as described in Example 7.

Example 11. Preparation of Polymorph Form I

Polymorph Form I of Icotinib phosphate was prepared by using the Volume ratio of H₂O and THF 1:30 (i.e., H₂O/THF 1:30, v/v) instead of 1:19 as Example 7 by following the same reaction conditions as described in Example 7.

Example 12. Preparation of Polymorph Form I

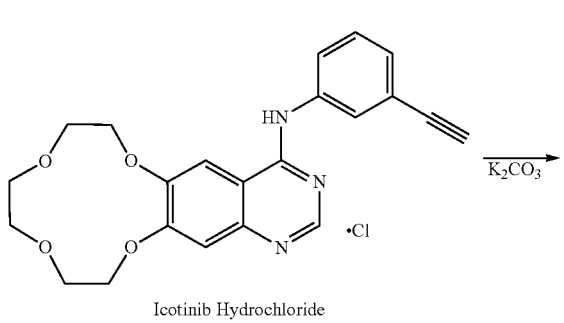

Icotinib Hydrochloride

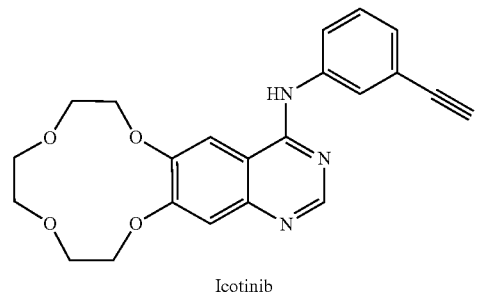

Icotinib 5 g Icotinib hydrochloride was dissolved in a mixture of 20 ml THF and 15 ml water, and then to this Icotinib solution was added a solution of 1.9 g potassium carbonate in 10 ml water dropped at 50° C. until the pH value of the reaction mixture reached 13. The reaction mixture was then stirred for 1-2 hrs before cooling down to the room temperature. The precipitate was filtered and washed with purified water and then dried for 8-10 hrs under vacuum at a temperature below 60° C. to produce 4 g Icontinib.

Polymorph Form I of Icotinib phosphate was obtained by reacting an Icontinib solution with a phosphoric acid solution (1:1 molar ratio) in H₂O/Acetone (1:19, v/v) at the room temperature. Detail procedures as following: 10 mg Icontinib was dissolved in 1 ml 2-butanone, 18.9 μL phosphoric acid was dissolved in 3 ml H₂O/Acetone (1:19, v/v) to obtain a 0.1 mol/L phosphoric acid solution. 0.26 ml of the 0.1 mol/L phosphoric acid solution was then added to the Icontinib solution. The reaction mixture was stirred for 24 hrs, and then the Polymorph Form I was isolated.

Example 13. Preparation of Polymorph Form I

Polymorph Form I was prepared by using the molar ratio of phosphoric acid and Icotinib 1.5:1 instead of 1:1 as Example 12 by following the same reaction conditions as described in Example 12.

Example 14. Preparation of Polymorph Form I

Polymorph Form I was prepared by using the molar ratio of phosphoric acid and Icotinib 2:1 instead of 1:1 as Example 12 by following the same reaction conditions as described in Example 12.

Example 15. Preparation of Polymorph Form I

Polymorph Form I of Icotinib phosphate was prepared by using the Volume ratio of H₂O and Acetone 1:10 (i.e., H₂O/Acetone 1:10, v/v) instead of 1:19 as Example 12 by following the same reaction conditions as described in Example 12.

Example 16. Preparation of Polymorph Form I

Polymorph Form I of Icotinib phosphate was prepared by using the Volume ratio of H₂O and Acetone 1:30 (i.e., H₂O/Acetone 1:30, v/v) instead of 1:19 as Example 12 by following the same reaction conditions as described in Example 12.

Example 17. Preparation of the Polymorph Form II

Polymorph Form II of Icotinib phosphate was prepared by reacting an Icontinib (from Example 1) solution with a solution of phosphoric acid (1:1 molar ratio) in IPA at the room temperature.

Detail procedures as following: 10 mg Icontinib was dissolved in 1 ml IPA. 18.9 μL phosphoric acid was dissolved in 3 ml IPA to obtain a 0.1 mol/L phosphoric acid solution. 0.26 ml of the 0.1 mol/L phosphoric acid solution was added to the Icontinib solution and the reaction mixture was stirred for 24 hrs, and then the Polymorph Form II was isolated.

Example 18. Preparation of Polymorph Form II

Polymorph Form II of Icotinib phosphate was prepared by using the molar ratio of phosphoric acid and Icotinib 1.5:1 instead of 1:1 as Example 17 by following the same reaction conditions as described in Example 17.

Example 19. Preparation of Polymorph Form II

Polymorph Form II of Icotinib phosphate was prepared by using the molar ratio of phosphoric acid and Icotinib 2:1 instead of 1:1 as Example 17 by following the same reaction conditions as described in Example 17.

Example 20. Preparation of Polymorph Form II

Polymorph Form II was prepared in the same manner (molar ratio 1:1) and according to the same procedure as provided in Example 17, except that IPA was replaced by acetone, and the Polymorph Form II of Icotinib phosphate was isolated.

Example 21. Preparation of Polymorph Form II

Polymorph Form II was prepared by using the molar ratio of phosphoric acid and Icotinib 1.5:1 instead of 1:1 as Example 20 by following the same reaction conditions as described in Example 20.

Example 22. Preparation of Polymorph Form II

Polymorph Form II was prepared by using the molar ratio of phosphoric acid and Icotinib in the reaction mixture to 2:1 instead of 1:1 as Example 20 by while following the same reaction conditions as described in Example 20.

Example 23. Preparation of Polymorph Form II

Polymorph Form II was prepared in the same manner (molar ratio 1:1) and according to the same procedure as provided in Example 17, except that IPA was replaced by ACN, and the Polymorph Form II isolated.

Example 24. Preparation of Polymorph Form II

Polymorph Form II was prepared by using the molar ratio of phosphoric acid and Icotinib 1.5:1 instead of 1:1 as Example 23 by following the same reaction conditions as described in Example 23.

Example 25. Preparation of Polymorph Form II

A ninth sample of Polymorph Form II was prepared by using the molar ratio of phosphoric acid and Icotinib 2:1 instead of 1:1 as Example 23 by following the same reaction conditions as described in Example 23.

Example 26. Preparation of Polymorph Form II

Polymorph Form II was prepared in the same manner (molar ratio 1:1) and according to the same procedure as provided in Example 17, except that IPA was replaced by 2-butanone, and the Polymorph Form II isolated Example 27. Preparation of Polymorph Form II Polymorph Form II was prepared by using the molar ratio of phosphoric acid and Icotinib 1.5:1 instead of 1:1 as Example 26 by following the same reaction conditions as described in Example 26.

Example 28. Preparation of Polymorph Form II

Polymorph Form II was prepared by using the molar ratio of phosphoric acid and Icotinib 2:1 instead of 1:1 as Example 26 by following the same reaction conditions as described in Example 26.

Example 29. Preparation of Polymorph Form II

Polymorph Form II was prepared in the same manner (molar ratio 1:1) and according to the same procedure as provided in Example 17, except that IPA was replaced by EtOH, and the Polymorph Form II isolated.

Example 30. Preparation of Polymorph Form II

Polymorph Form II was prepared by using the molar ratio of phosphoric acid and Icotinib 1.5:1 instead of 1:1 as Example 29 by following the same reaction conditions as described in Example 29.

Example 31. Preparation of Polymorph Form II

Polymorph Form II was prepared by using the molar ratio of phosphoric acid and Icotinib 2:1 instead of 1:1 as Example 29 by following the same reaction conditions as described in Example 29.

Example 32. Preparation of Polymorph Form III

Anti-solvent crystallization from DMSO/EtOAc was carried out by dissolving 10 mg of Polymorph Form II in DMSO to obtain a saturated solution. EtOAc was added to the saturated solution to induce precipitation. The resulting solution was stirred for 24 hrs, and the Polymorph Form III was isolated.

Example 33. Preparation of Polymorph Form III

Reversed anti-solvent crystallization from DMSO/EtOAc was carried out by dissolving 10 mg Polymorph Form II in DMSO to obtain a saturated solution followed by addition of the saturated solution into 5 ml EtOAc to induce precipitation. The resulting solution was stirred for 24 hrs, and the Polymorph Form III was isolated.

Example 34. Preparation of Polymorph Form III

Vapor diffusion method from DMSO/IPAc was performed by dissolving 10 mg of Polymorph Form II into DMSO to get a saturated solution in a 3 ml glass vial. The 3 ml glass vial then was sealed into a 20 ml glass vial containing 4 ml IPAc, and was left to induce precipitation at RT and the Polymorph Form III was isolated.

Example 35. Preparation of Polymorph Form III

Vapor diffusion method from DMSO/MTBE was performed by dissolving 10 mg of Polymorph Form II into DMSO to get a saturated solution in a 3 ml glass vial. The 3 ml glass vial then was sealed into a 20 ml glass vial containing 4 ml MTBE, and was left to induce precipitation at RT and the Polymorph Form III was isolated.

Example 36. Preparation of Polymorph Form IV

Anti-solvent crystallization from DMF/DCM was carried out by dissolving 10 mg of Polymorph Form II in DMF to obtain a saturated solution. DCM was added to the saturated solution to induce precipitation. The resulting solution was stirred for 24 hrs, and the Polymorph Form IV was isolated.

Example 37. Pharmacokinetic Study of Icotinib Hydrochloride and Polymorph Form II of Icotinib Phosphate Drugs and reagents: The Icotinib hydrochloride used in this study was of Crystalline Form I disclosed by the WO2010/003313. Polymorph Form II of Icotinib phosphate and Icotinib hydrochloride were ground to fine particles. The material content (purity) was not less than 99.0%. Sodium carboxymethyl cellulose was medical supply graded.

Experimental animals: SD rats were divided to an Icotinib hydrochloride group and a Polymorph Form II group, with both groups consisting of half males and half females.

Pharmaceutical preparation: the amount of each compound was weighed and then sodium carboxymethyl cellulose was added to result in the test compound's concentration of 0.5%. The solid mixture was then added to prepare a suspension thereof at a final concentration of 10 mg/ml in water.

Administration and sample collection: each suspension was administered orally to fasted SD rats at a dose equivalent to 50 mg/kg Icotinib in a dose volume of 5 ml/kg. 0.4 ml of blood was collected in EDTA-K pre anticoagulant tubes at time intervals of 0.5, 1, 1.5, 2, 4, 6, 8 and 24 hrs after the administration of the test compound, centrifuged at 3000 rpm for 10 minutes, and 120 μL plasma was collected and kept in cold storage.

Figure 5:
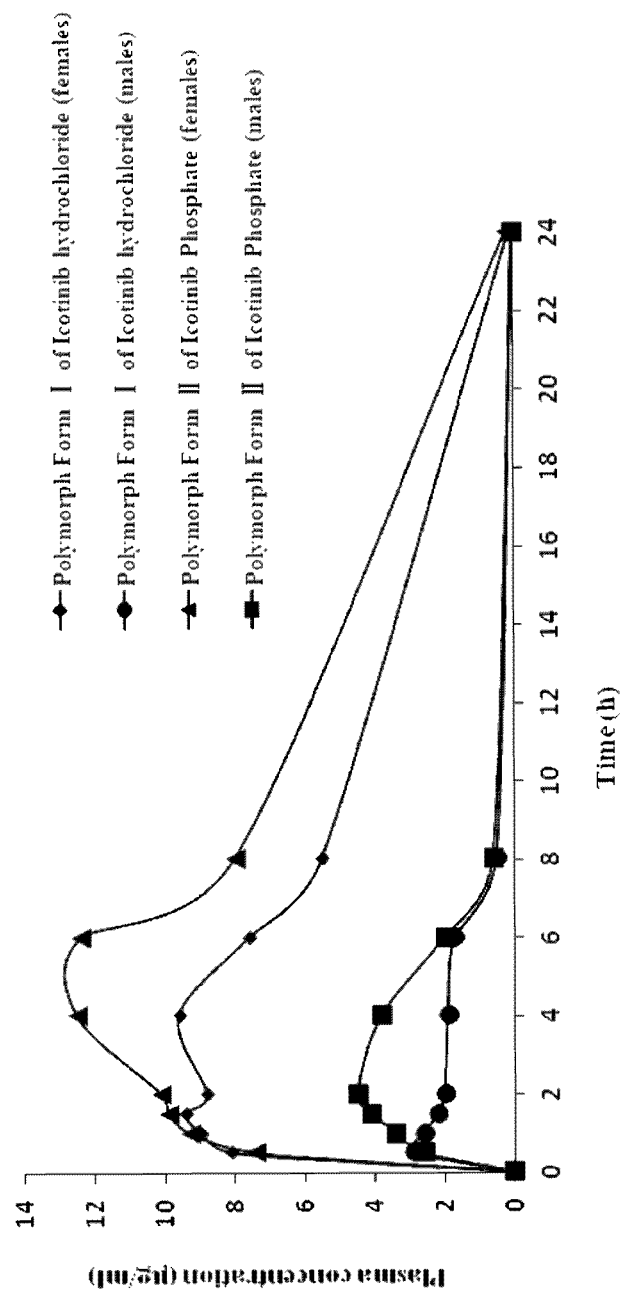
FIG. 5: The plasma concentration-time curves of Crystalline Form I Icotinib hydrochloride and Polymorph Form II of the compound of Formula I.

Samples were analyzed by high performance liquid chromatography. The chromatographic conditions utilized C18-silane bonded silica as stationary phase, 0.02 mol/L of sodium dihydrogen phosphate in acrylonitrile (40:60, using sodium hydroxide solution to adjust pH to 5.0) as the mobile phase and a detection wavelength of 334 nm. PK profile comparison of Crystalline Form I of Icotinib Hydrochloride and Polymorph Form II of Icotinib phosphate was summarized in Table 1 and FIG. 5. Polymorph Form II of Icotinib phosphate showed higher bioavailability than Crystalline Form I of Icotinib hydrochloride.

TABLE 1

|  |  | $AUC_{(0-24)}$ (mg/L*h) | $AUC_{(0-\infty)}$ (mg/L*h) | $T_{1/2}$ (h) | $T_{max}$ (h) | $C_{max}$ (mg/L) |
|---|---|---|---|---|---|---|
| Icotinib hydrochloride crystalline form I | females | 113.0 ± 24.0 | 123.6 ± 13.0 | 6.2 ± 3.5 | 3.0 ± 1.7 | 10.2 ± 1.9 |
|  | males | 19.0 ± 7.1 | 19.1 ± 7.2 | 2.9 ± 0.4 | 2.3 ± 3.2 | 3.4 ± 0.4 |
| Icotinib Phosphate polymorph form II | females | 155.2 ± 20.2 | 156.7 ± 17.8 | 2.9 ± 0.4 | 4.7 ± 1.2 | 13.1 ± 2.4 |
|  | males | 28.6 ± 8.1 | 28.7 ± 8.1 | 2.6 ± 0.2 | 2.3 ± 1.5 | 4.9 ± 0.8 |

Example 38. Formulation of a Hard Gel Capsule

As a specific embodiment of an oral composition, about 100 mg of the Polymorph Form of Examples 1-37 is formulated with sufficient finely divided lactose to provide a total amount of about 580 mg to about 590 mg to fill a size 0 hard gel capsule.

Although the present invention has been fully described in connection with embodiments thereof with reference to the accompanying drawings, it is to be noted that various change and modifications will become apparent to those skilled in the art. Such changes and modifications are to be understood as being included within the scope of the present invention as defined by the appended claim.

What is claimed is:

1. A polymorph form of a compound of Formula I:

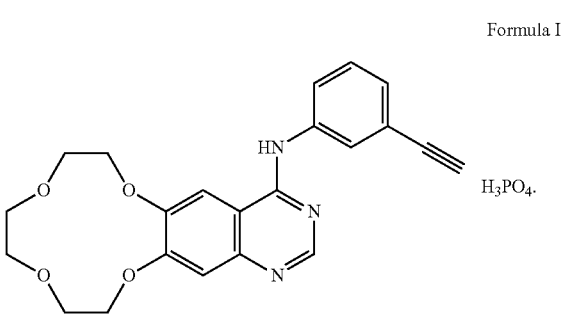

Formula I

2. The polymorph form of claim 1, wherein the polymorph form is of Polymorph Form I with an X-ray powder diffraction pattern having characteristic peaks at diffraction angles 2θ of 6.4°, 8.4°, 12.8°, 14.4° and 19.0°±0.2°.

3. The polymorph form of claim 2, wherein the X-ray powder diffraction pattern has characteristic peaks at diffraction angles 2θ of 6.4°, 8.4°, 12.8°, 14.4°, 19.0°, 20.7°, 22.7° and 25.7°±0.2°.

4. The polymorph form of claim 2, wherein the X-ray powder diffraction pattern is shown as in FIG. 1.

5. The polymorph form of claim 1, wherein the polymorph form is of Polymorph Form II with an X-ray powder diffraction pattern having characteristic peaks at diffraction angles 2θ of 7.4°, 13.8°, 14.8°, 16.4° and 18.0°±0.2°.

6. The polymorph form of claim 5, wherein the X-ray powder diffraction pattern has characteristic peaks at diffraction angles 2θ of 7.4°, 13.8°, 14.8°, 16.4°, 18.0°, 20.2°, 22.1° and 23.5°±0.2°.

Figure 2:
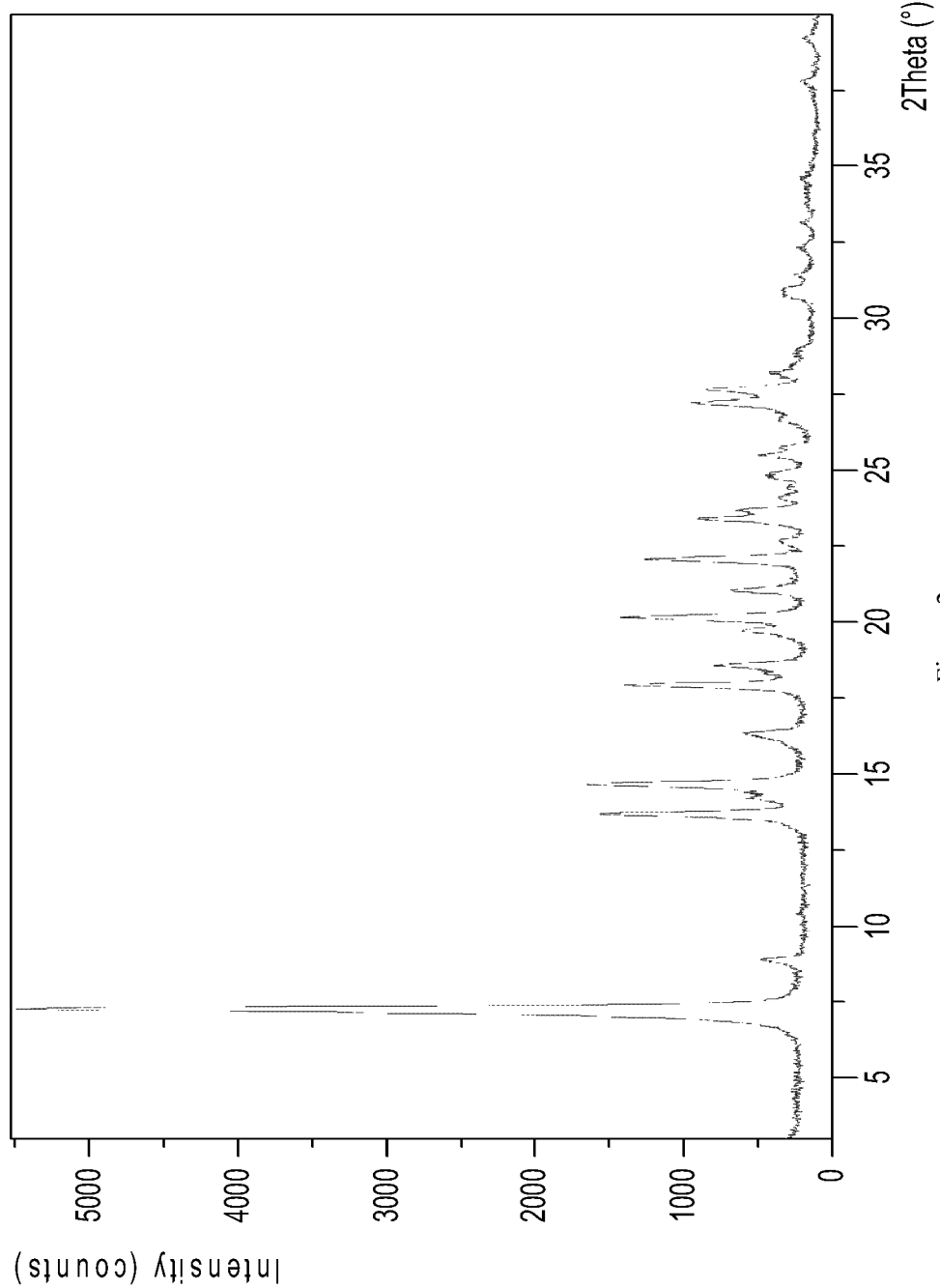
FIG. 2: The X-ray powder diffraction pattern of Polymorph Form II of the compound of Formula I.

7. The polymorph form of claim 5, wherein the X-ray powder diffraction pattern is shown as in FIG. 2.

8. The polymorph form of claim 1, wherein the polymorph form is of Polymorph Form III with an X-ray powder diffraction pattern having characteristic peaks at diffraction angles 2θ of 5.4°, 7.9°, 13.1°, 16.2° and 18.6°±0.2°.

9. The polymorph form of claim 8, wherein the X-ray powder diffraction pattern has characteristic peaks at diffraction angles 2θ of 5.4°, 7.9°, 13.1°, 162°, 18.6°, 19.7°, 20.9° and 24.0°±0.2°.

Figure 3:
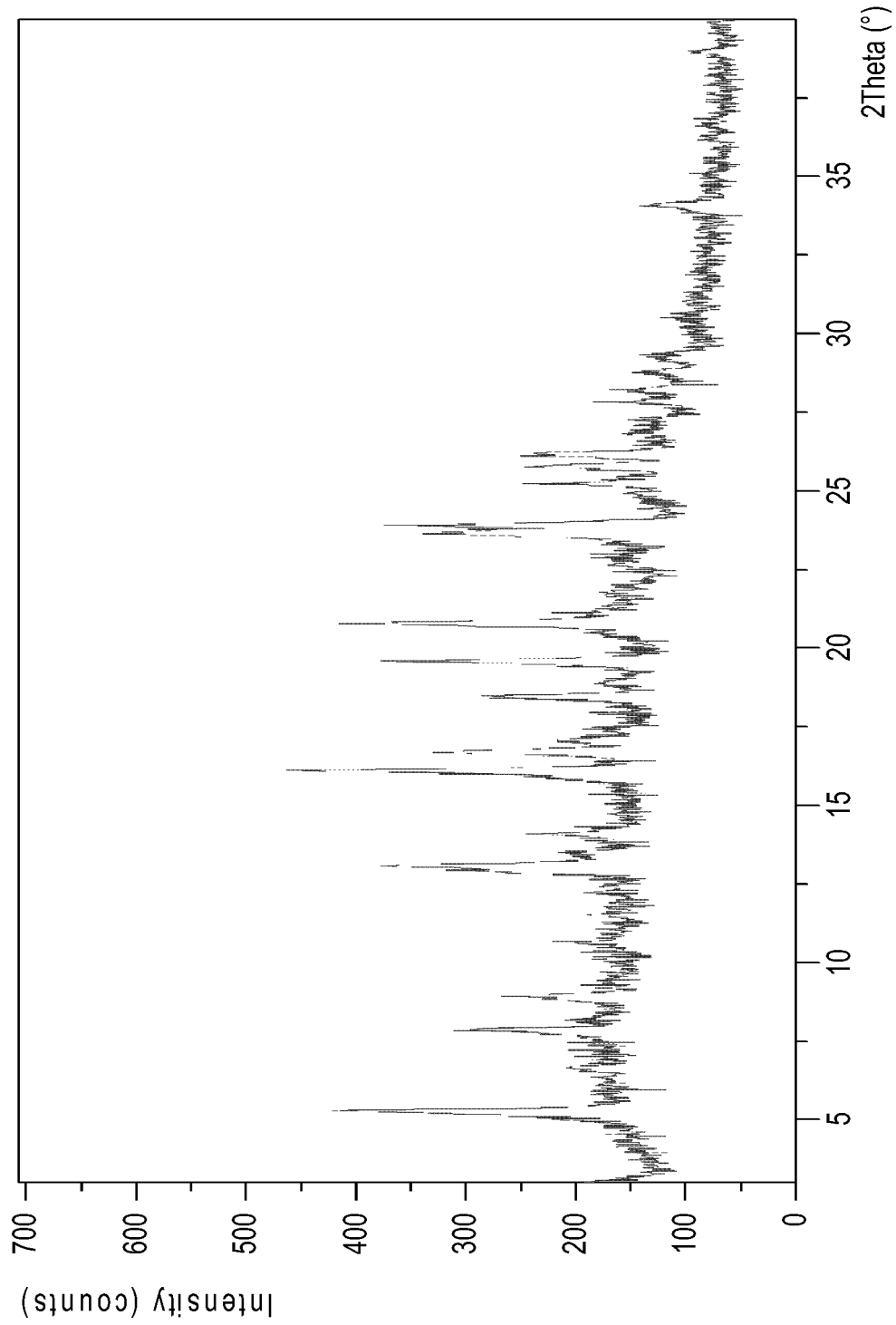
FIG. 3: The X-ray powder diffraction pattern of Polymorph Form III of the compound of Formula I.

10. The polymorph form of claim 8, wherein the X-ray powder diffraction pattern is shown as in FIG. 3.

11. The polymorph form of claim 1, wherein the polymorph form is of Polymorph Form IV with an X-ray powder diffraction pattern having characteristic peaks at diffraction angles 2θ of 6.1°, 8.0°, 14.7°, 17.3° and 18.3°±0.2°.

12. The polymorph form of claim 11, wherein the X-ray powder diffraction pattern has characteristic peaks at diffraction angles 2θ of 6.1°, 8.0°, 14.7°, 17.3°, 18.3°, 20.2°, 21.3° and 23.8°±0.2°.

Figure 4:
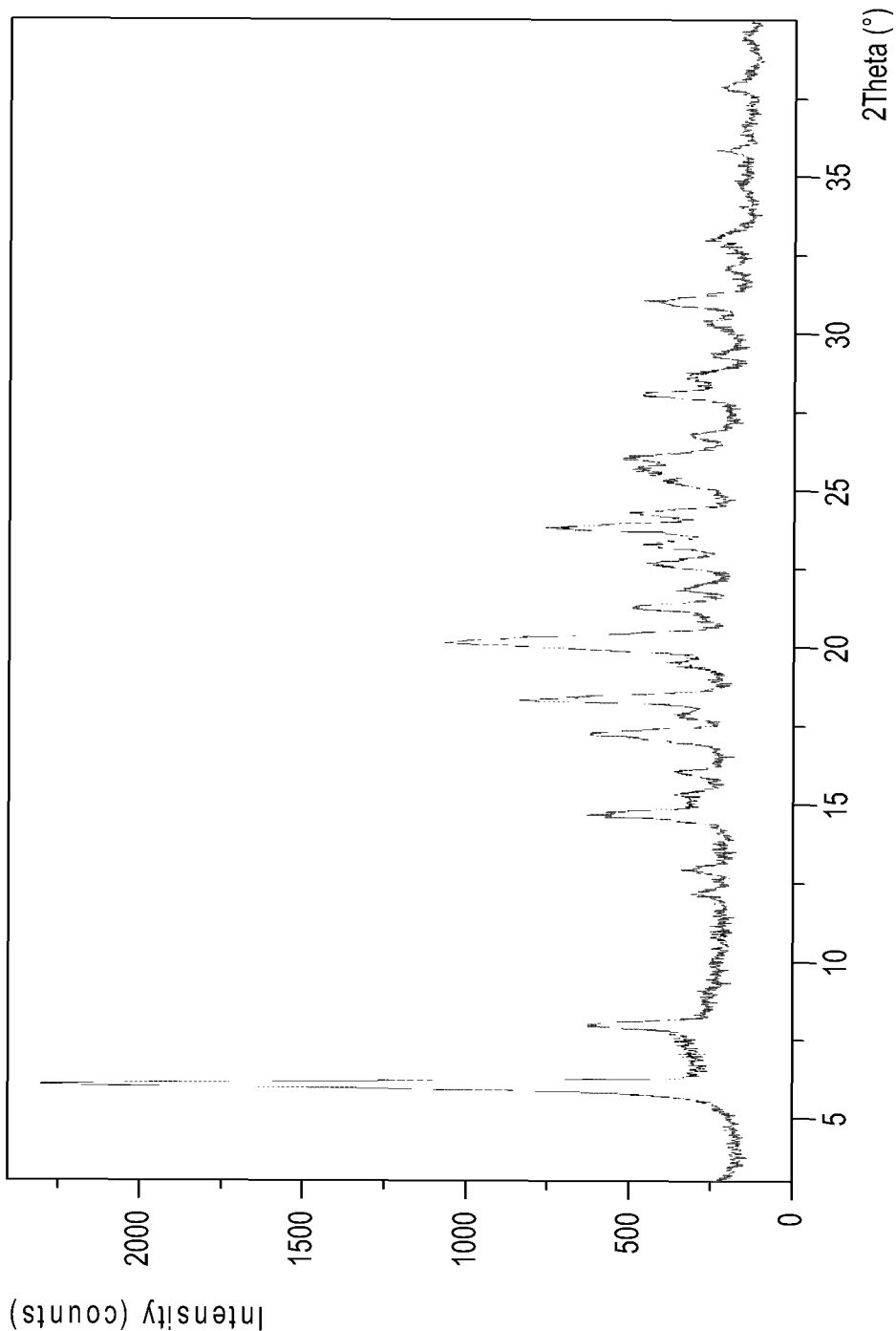
FIG. 4: The X-ray powder diffraction pattern of Polymorph Form IV of the compound of Formula I.

13. The polymorph form of claim 11, wherein the X-ray powder diffraction pattern is shown as in FIG. 4.

14. A process of preparing a polymorph form of claim 1, comprising:
    a). reactive crystallization of the Icotinib solution with solutions of phosphoric acid in THF, Dioxane, H₂O/THF, or H₂O/Acetone to obtain a Polymorph Form I of the compound of Formula I with an X-ray powder diffraction pattern having characteristic peaks at diffraction angles 2θ of 6.4°, 8.4°, 12.8°, 14.4° and 19.0°±0.2°; or
    b). reactive crystallization of the Icotinib solution with solutions of phosphoric acid in IPA, Acetone, ACN, 2-Butanone, or EtOH to obtain a Polymorph Form II of the compound of Formula I with an X-ray powder diffraction pattern having characteristic peaks at diffraction angles 2θ of 7.4°, 13.8°, 14.8°, 16.4° and 18.0°±0.2°; or
    c). at least one step chosen from reverse anti-solvent or anti-solvent crystallization from DMSO/EtOAc, vapor diffusion from DMSO/IPAc or DMSO/MTBE to obtain a Polymorph Form III of the compound of Formula I with an X-ray powder diffraction pattern having characteristic peaks at diffraction angles 2θ of 5.4°, 7.9°, 13.1°, 16.2° and 18.6°±0.2°; or
    d). at least one step chosen from anti-solvent crystallization from DMF/DCM to obtain a Polymorph Form IV of the compound of Formula I with an X-ray powder diffraction pattern having characteristic peaks at diffraction angles 2θ of 6.1°, 8.0°, 14.7°, 17.3° and 18.3°±0.2°.

15. The process of claim 14, wherein:
(a). the temperature of step a), b), c) or d) is room temperature; or
(b). the volume ratio of $H_2O$ and THF, or $H_2O$ and Acetone of step a) ranges from 1:10 to 1:30; or
(c) the molar ratio between phosphoric acid and Icotinib of step a) or b) ranges from 1:1 to 2:1.

16. The process of claim 14, wherein the molar ratio between phosphoric acid and Icotinib is 1:1.

17. The process of claim 14, wherein the step c) or d), comprises:
(i). dissolving Icotinib phosphate in DMSO to obtain a saturated solution, adding EtOAc to the saturated solution, stirring the resulting solution for at least 2 hrs and isolating the Polymorph Form III of the compound of Formula I; or
(ii). dissolving Icotinib phosphate in DMSO to obtain a saturated solution, adding the saturated solution into EtOAc, stirring the resulting solution for at least 2 hrs and isolating the Polymorph Form III of the compound of Formula I; or
(iii). dissolving Icotinib phosphate into DMSO to get a saturated solution in a first container, placing the first container in a second container containing IPAc or MTBE, and inducing precipitation to obtain the Polymorph Form III of the compound of Formula I; or
(iv) dissolving Icotinib phosphate in DMF to obtain a saturated solution, adding DCM to the saturated solution, stirring the resulting solution for at least 2 hrs and isolating the Polymorph Form IV of the compound of Formula I.

18. A pharmaceutical composition comprising a therapeutically effective amount of the polymorph form of claim 1 and a pharmaceutically acceptable excipient, adjuvant or carrier.

19. The pharmaceutical composition of claim 18, wherein the polymorph form has a purity of ≥85 wt %.

20. The pharmaceutical composition of claim 18, wherein the polymorph form has a purity of ≥99 wt %.

21. The pharmaceutical composition of claim 18, comprising at least one of additional active ingredient.

22. The pharmaceutical composition of claim 18, wherein the pharmaceutical composition is suitable for oral administration.

23. The pharmaceutical composition of claim 18, wherein the pharmaceutical composition is in a form of tablet or capsule.

24. The pharmaceutical composition of claim 18, wherein the composition comprises 0.01 wt %-99 wt % of the polymorph form.

25. The pharmaceutical composition of claim 24, wherein the composition comprises 10 wt %-50 wt % of the polymorph form.

* * * * *